(12) United States Patent
Turk et al.

(10) Patent No.: US 9,951,233 B2
(45) Date of Patent: Apr. 24, 2018

(54) ENVIRONMENTALLY FRIENDLY COALESCING AGENTS

(75) Inventors: Brian Turk, San Clemente, CA (US); Michael Mang, Newton, MA (US)

(73) Assignee: Myriant Corporation, Woburn, MA (US)

( * ) Notice: Subject to any disclaimer, the term of this patent is extended or adjusted under 35 U.S.C. 154(b) by 86 days.

(21) Appl. No.: 14/126,367

(22) PCT Filed: Mar. 26, 2012

(86) PCT No.: PCT/US2012/030553
§ 371 (c)(1),
(2), (4) Date: Mar. 28, 2014

(87) PCT Pub. No.: WO2012/173679
PCT Pub. Date: Dec. 20, 2012

(65) Prior Publication Data
US 2014/0243446 A1    Aug. 28, 2014

Related U.S. Application Data

(60) Provisional application No. 61/497,417, filed on Jun. 15, 2011.

(51) Int. Cl.
| | |
|---|---|
| C09D 7/12 | (2006.01) |
| C07C 69/40 | (2006.01) |
| C09D 125/06 | (2006.01) |
| C09D 125/14 | (2006.01) |
| C09D 131/04 | (2006.01) |
| C09D 133/08 | (2006.01) |
| C09D 163/00 | (2006.01) |
| C09D 167/00 | (2006.01) |
| C08K 5/11 | (2006.01) |
| C09D 7/00 | (2018.01) |
| G03G 9/08 | (2006.01) |
| C09D 11/00 | (2014.01) |
| C09D 5/00 | (2006.01) |

(52) U.S. Cl.
CPC .............. C09D 7/001 (2013.01); C07C 69/40 (2013.01); C09D 5/00 (2013.01); C09D 7/1233 (2013.01); C09D 11/00 (2013.01); G03G 9/0804 (2013.01); C08K 5/11 (2013.01); C09D 125/06 (2013.01); C09D 125/14 (2013.01); C09D 131/04 (2013.01); C09D 133/08 (2013.01); C09D 163/00 (2013.01); C09D 167/00 (2013.01)

(58) Field of Classification Search
CPC .................... C08K 5/11; C07C 69/40
See application file for complete search history.

(56) References Cited

U.S. PATENT DOCUMENTS

| | | | |
|---|---|---|---|
| 3,399,158 A | 8/1968 | Huitson | |
| 4,525,512 A | 6/1985 | Hudson | |
| 5,834,150 A * | 11/1998 | Brennan | G03G 9/08797 430/109.3 |
| 6,210,693 B1 | 4/2001 | Inoue | |
| 6,797,753 B2 * | 9/2004 | Benecke | C08K 5/0016 524/114 |
| 8,106,239 B2 | 1/2012 | Zhou | |
| 8,586,777 B2 | 11/2013 | Zhou | |
| 9,034,965 B2 * | 5/2015 | Kazemizadeh | C08K 5/0016 524/114 |
| 9,080,032 B2 | 7/2015 | Facklam | |
| 2004/0071953 A1 | 4/2004 | Sobieski | |
| 2006/0173110 A1 * | 8/2006 | Baba | C09D 175/04 524/386 |
| 2009/0149591 A1 * | 6/2009 | Yang | C09D 5/024 524/418 |
| 2009/0198002 A1 | 8/2009 | Zhou | |
| 2012/0095145 A1 | 4/2012 | Zhou | |

FOREIGN PATENT DOCUMENTS

| | | | |
|---|---|---|---|
| EP | 0026982 A1 | 4/1981 | |
| FR | 2296657 A1 | 7/1976 | |
| WO | 2009097142 A1 | 8/2009 | |
| WO | 2012054317 A1 | 4/2012 | |
| WO | WO 2012079231 A1 * | 6/2012 | C08K 5/11 |

OTHER PUBLICATIONS

Stuart (Poly(vinyl chloride) plasticized with succinate esters: synthesis and characterization. Polym Bull. 2010, 65, pp. 589-598).*

* cited by examiner

*Primary Examiner* — Brieann R Johnston
(74) *Attorney, Agent, or Firm* — Ramasamy M. Mannan

(57) ABSTRACT

A composition may include a binder; a coalescing agent with the general formula of

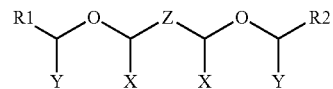

wherein Z is $C_1$-$C_{10}$, wherein X is —H and Y is =O or X is =O and Y is —H or —$CH_3$, and wherein R1 and R2 are independently selectable and comprise a $C_1$-$C_{12}$ or derivative thereof; and a solvent. The composition may be used in products like a paint, a coating, an adhesive, an ink, a toner, a sealant, a stain, a glaze, a carpet backing, and a primer.

16 Claims, No Drawings

ENVIRONMENTALLY FRIENDLY COALESCING AGENTS

The application is the U.S. national stage application of International Patent Application No. PCT/US2012/030553, which claims the priority of the U.S. Provisional Application Ser. No. 61/497,417, filed on Jun. 15, 2011.

BACKGROUND

The present invention relates to coalescing agents for paints, coatings, adhesives, and the like that can be used in a myriad of applications including, but not limited to, carpet backing, industrial coatings, architectural coatings, exterior insulating finishing systems, traffic paint, roof coatings, craft paints, paper coatings, and fiber coatings.

Coating compositions are used for a variety of applications, typically for the decoration or protection of surfaces. The coating compositions contain binders, typically emulsion polymers (e.g., latex), maintained in liquid solvents. Upon application of the coating materials, the solvents evaporate and the binders harden into a mechanically rigid state while binding pigments, fillers, and other additives.

Due to environmental concerns, among other things, there has been a movement toward reducing the amount of volatile organic compounds (VOCs) in paints, stains, and other coating compositions. However, some of the desirable properties of the coating compositions, like durability, opaqueness, and speed of drying, have been negatively affected by the absence of VOCs in those compositions. Companies have recently been searching for formulations and methods of making coating compositions with a low VOC content to meet new and developing regulations, while maintaining good physical properties in the final product.

The primary source of VOCs in paints is the coalescing agents. A coalescing agent functions as a solvent as well as a plasticizer for the polymer particles and assists in formation of a coherent film from the dispersed polymer phase in a typical waterborne formulation after the formulation is applied to a surface and allowed to dry. A desirable coalescing agent will allow formation of a film quickly and at a broad range of application temperatures for many different types of polymeric binder systems, meet the regulatory standards for VOC emissions, and allow the coating film to develop useful physical properties soon after application.

Because governments have established regulations setting forth guidelines relating to the amount of VOCs that may be released into the atmosphere, a need for low VOC coalescing agents that can be used in coating compositions such that desirable properties, like stability, compatibility, and film formation ability, are not compromised in the applied coating. Additionally, coalescing agents with these characteristics that are produced from renewable sources like grain and corn would be further advantageous as society reduces consumption of petroleum.

SUMMARY OF THE INVENTION

The present invention relates to coalescing agents for paints, coatings, adhesives, and the like that can be used in a myriad of applications including, but not limited to, carpet backing, industrial coatings, architectural coatings, exterior insulating finishing systems, traffic paint, roof coatings, craft paints, paper coatings, and fiber coatings.

In some embodiments, the present invention provides a composition comprising: a binder; a coalescing agent derived from microbial fermentation of carbohydrates with the general formula of Formula I (below) where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof; and a solvent.

In other embodiments, the present invention provides a product comprising: a composition comprising: a binder; a coalescing agent with the general formula of Formula I (below) where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof; and a solvent; wherein the product is selected from the group consisting of a paint, a coating, an adhesive, an ink, a toner, a sealant, a stain, a glaze, a carpet backing, and a primer.

In still other embodiments, the present invention provides a method comprising: providing a composition that comprises: a coalescing agent with the general formula of Formula I (below), where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof; and a binder; and a solvent; and applying the composition to a surface so as to form a coating.

The features and advantages of the present invention will be readily apparent to those skilled in the art upon a reading of the description of the preferred embodiments that follows.

DETAILED DESCRIPTION

The present invention relates to coalescing agents for paints, coatings, adhesives, and the like that can be used in a myriad of applications including, but not limited to, carpet backing, industrial coatings, architectural coatings, exterior insulating finishing systems, traffic paint, roof coatings, and craft paints, paper coatings, and fiber coatings.

Of the many advantages the present invention provides low VOC coalescing agents that can be produced from renewable sources, e.g., corn, wheat, tapioca, rice, sorghum, or lignocellulosics. Production of coalescing agents from renewable resources that are a low VOC synergistically provide for an environmentally friendly coating in both the production and implementation steps. Further, the final coatings produced from coating formulations containing the low VOC coalescing agents may demonstrate greater hiding power, i.e., opaqueness; cleaner, whiter films; increased hardness; increased block resistance; decreased dirt pickup; decreased minimum film forming temperature; decreased usage requirements; decreased odor; and faster drying to a harder film relative to traditional coating formulations.

In some embodiments, a coating formulation may comprise, consist essentially of, or consist of a coalescing agent, a solvent, and a binder. Optionally, other additives may be included, for example, a pigment, a pigment extender, a colorant, a tint, a dye, a surfactant, a suspension additive, an antifoaming agent, a biocide, a fungicide, a particulate, a cementitious composition, a texturizing composition, a water-miscible solvent, a pH adjuster, a crosslinking agent, a thickening agent, a viscosifier, a filler, a freeze-thaw additive, a flattening additive, a pigment grind additive, an opacifier, a stabilizer, a film preservative, and any combination thereof. In some embodiments, a coating formulation may comprise more than one coalescing agent.

In some embodiments, a coalescing agent of the present invention may have the general chemical structure of

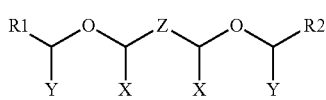

Formula I where Z can be $C_1$-$C_{10}$, where (i) X is —H and Y is =O, or (ii) X is =O and Y is —H or —$CH_3$, and where R1 and R2 are independently selectable and comprise a $C_1$-$C_{12}$ or derivative thereof. For simplicity and clarity herein, "R" will be used to generically refer to the chemical structures that R1 and R2 can be (simultaneously or individually). In some embodiments, R1 and R2 are independently selectable and therefore may be different.

Without being bound by theory or mechanism, it is believed that Z, R1, and R2 may affect, among other things, the properties of the coalescing agent like volatility, solubility, freezing point, and odor; the interaction between the coalescing agent and other coating formulation components; and the properties of the final coating like thickness, durability, flexibility, toughness, opaqueness or hiding effectiveness, finish, freezing point, block resistance, scrub resistance, pigment brilliance, odor, and hydrophobicity.

In some embodiments, Z may be linear. In some embodiments, Z may be branched. In some embodiments, Z may comprise at least one unsaturated C—C bond. In some embodiments, Z may comprise at least one cyclic group. In some embodiments, Z may comprise at least one aromatic group. In some embodiments, Z may be a combination of the foregoing. By way of nonlimiting example, coalescing agents of the present invention may be a di-ester derivative of a dicarboxylic acid (e.g., succinic acid, adipic acid, sebacic acid, malonic acid, glutaric acid, pimelic acid, suberic acid, azelaic acid, ortho-phthalic acid, iso-phthalic acid, tere-phthalic acid, maleic acid, fumaric acid, glutaconic acid, traumatic acid, muconic acid, and the like), a diol (e.g., 1,4-butanediol, resorcinol, and the like), or any derivative thereof.

In some embodiments, R may be a linear carbon chain or derivative thereof. In some embodiments, the linear carbon chain may include one or more double and/or triple carbon-carbon bonds. By way of nonlimiting example, at least one R group may be a linear carbon chain with a terminal vinyl group.

In some embodiments, R may be a linear carbon chain or derivative thereof such that the R group is bonded to Formula I on a interior carbon so as to form a branched structure. In some embodiments, a linear carbon chain R group with an interior bond to Formula I may comprise $C_3$-$C_{12}$, including any subset therebetween (e.g., $C_4$-$C_{12}$, $C_7$-$C_{10}$, or $C_6$-$C_{10}$). By way of nonlimiting example, when X is =O, Y is —H, Z is $C_2$, and R1 and R2 are 3-heptyl ($C_7$ with an internal attachment point at the C3 position), the coalescing agent of the present invention is bis(2-ethylhexyl)succinate shown in Formula II below.

In some embodiments, R may be branched including, but not limited to, isobutyl, t-butyl, 2-ethylhexyl, and the like. In some embodiments, the branched carbon chain may include one or more double and/or triple carbon-carbon bonds. In some embodiments, a branched R may have in total at least $C_3$, at least $C_4$, at least $C_5$, at least $C_6$, or at least $C_7$. In some embodiments, a branched R may have in total $C_3$-$C_{12}$, including any subset therebetween (e.g., $C_7$-$C_{10}$). In some embodiments, coalescing agents according to Formula I with at least one branched R may provide for a coating composition with a lower freezing point, which may advantageously make available storage and transport in lower temperature environments.

In some embodiments, R may include a cyclic carbon structure or derivative thereof. By way of nonlimiting example, R may be —($C_6H_{11}$), —$CH_2$($C_6H_{11}$), or —$CH_2CH_2$($C_6H_{11}$). In some embodiments, R may be an aromatic derivative including, but not limited to, —($C_6H_5$), —$CH_2$($C_6H_5$), and —$CH_2CH_2$($C_6H_5$).

In some embodiments, R may have at least one heteroatom. Examples of suitable heteroatoms include, but are not limited to, nitrogen, oxygen, phosphorous, sulfur, fluorine, chlorine, bromine, iodine, and any combination thereof. In some embodiments, R may have at least one heteroatom within the carbon chain or as a branch of the carbon chain. By way of nonlimiting example, R may include a polyethylene oxide chain like —$CH_2OCH_2OCH_2OCH_2OH$ or a polypropylene oxide chain as R itself or as a branch of a linear carbon chain.

In some embodiments, R may have at least one reactive group. Examples of suitable reactive groups include, but are not limited to, olefins, carboxylic acids, alcohols, epoxides, cyanates, amines, silanes, epoxy-silanes, heteroatoms, and any combination thereof. In some embodiments, R may include a reactive group that is capable of reacting via an addition reaction, a condensation reaction, a ring-opening reaction, a free-radical reaction, and any combination thereof. One nonlimiting example may include an R with a terminal amine that can undergo a condensation reaction with a carboxylic acid. Another nonlimiting example may be an R of —$(CH_2)_3CH=CH_2$ that can react with a binder compound containing an olefin via a free-radical reaction.

It should be noted that within the scope of the present invention are R groups with one or more of the characteristics included herein (e.g., linear with a terminal or internal bond to Formula I, branched, cyclic, aromatic, include an unsaturated bond, include heteroatoms, include a reactive group, or a combination thereof). By way of nonlimiting example, an R group may comprise an aromatic ring and a heteroatom. By way of another nonlimiting example, an R group may comprise a branched carbon chain and a reactive group.

It should be noted that when "about" is provided at the beginning of a numerical list, "about" modifies each number of the numerical list. It should be noted that in some numerical listings of ranges, some lower limits listed may be greater than some upper limits listed. One skilled in the art will recognize that the selected subset will require the selection of an upper limit in excess of the selected lower limit.

In some embodiments, R1 and R2 may be independently chosen such that molecular weight of the resultant coalescing agent may range from a lower limit of about 150 amu, 200 amu, 300 amu, 325 amu, 350 amu, or 400 amu to an upper limit of about 750 amu, 700 amu, 650 amu, 600 amu, or 500 amu, and wherein the molecular weight may range Formula II

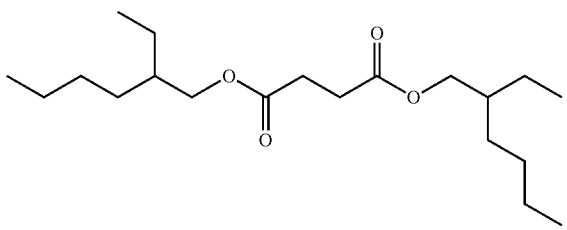

from any lower limit to any upper limit and encompass any subset between the upper and lower limits.

In some embodiments, R1 and R2 may be independently chosen such that the resultant coalescing agent may be characterized as a low volatile organic content "low VOC" coalescing agent. As used herein, "low VOC" should be taken to mean a VOC of not more than about 250 g/L (about 25% w/v), preferably not more than about 150 g/L (about 15% w/v), more preferably not more than about 100 g/L (about 10% w/v), most preferably not more than about 50 g/L (about 5% w/v), for example, not more than about 30 g/L (about 3% w/v) or not more than about 20 g/L (about 2% w/v). As referred to herein, VOCs are defined according to U.S. Environmental Protection Agency (EPA) Method 24. Low VOC compositions can also include "zero-VOC" compositions, which can advantageously have a VOC content of not more than about 10 g/L (about 1% w/v), preferably not more than about 8 g/L (about 0.8% w/v), more preferably not more than about 5 g/L (about 0.5% w/v), for example, not more than about 2 g/L (about 0.2% w/v).

In some embodiments, R1 and R2 may be independently chosen such that the resultant coalescing agent has a boiling point ranging from a lower limit of about 250° C., 300° C., or 350° C. to an upper limit of about 450° C., 400° C., or 350° C., wherein the boiling point may range from any lower limit to any upper limit and encompass any subset between the upper and lower limits.

In some embodiments, a coalescing agent of the present invention may be formed by the reaction of a diol and a carboxylic acid, or by the reaction of a diacid and an alcohol. In some embodiments, a diol and/or a carboxylic acid, or a diacid and/or an alcohol, used to form a coalescing agent of the present invention may be bioderived. Bioderived reactants may advantageously provide for a coalescing agent of the present invention that is not only low VOC but also bio-based, which together may be advantageous for providing compositions (e.g., paints, coatings, and the like including other applications described herein) that meet more stringent environmental certification requirements.

In some embodiments, a coalescing agent with Formula I where Z is $C_2$, X is —H, and Y is =O may generally be formed from the precursor of 1,4-butanediol. To achieve the coalescing agent, 1,4-butanediol may be reacted with a carboxylic acid via esterification, with an acyl chloride or acid anhydride via alcoholysis, or with an alkene in the presence of a metal carbonyl catalyst via hydroesterification. The precursor of 1,4-butanediol may be obtained from any source including, but not limited to, renewable feedstocks like corn, wheat, tapioca, rice, sorghum, or lignocellulosics (such as corn stover, rice hulls, wheat straw, wood pulp, and the like) and any combination thereof. The carboxylic acid may be obtained from renewable feedstocks.

In some embodiments, a coalescing agent with Formula I where Z is $C_2$, X is =O, and Y is —H or —$CH_3$ may generally be formed from the precursor of succinic acid. To achieve the coalescing agent, succinic acid may be reacted with an alcohol or a diazo derivative via esterification or with an olefin in the presence of a palladium-based catalyst. The succinic acid may be obtained from any source including, but not limited to, renewable feedstocks like corn, wheat, tapioca, rice, sorghum, or lignocellulosics such as corn stover, rice hulls, wheat straw, wood pulp, and the like and any combination thereof.

A preferred method for the preparation of succinic acid may be to use microbial fermentation of carbohydrates derived from grains or starchy tubers, or from the hydrolysate of delignified lignocellulosic agricultural waste products, followed by the separation and purification of the product of fermentation. Preferred sources of carbohydrates may include corn, sorghum, tapioca, cassava, or sweet potato. Preferred agricultural waste products may include corn stover, rice hull, wheat straw, and wood pulp. The succinic acid so obtained may be converted into 1,4-butanediol using catalytic hydrogenation using well known industrial processes for the preparation of butanediol including the Davy-Kvaerner process or the Lurgi-Geminox process.

In some embodiments, the coalescing agent may be present in the coating formulation in an amount that may range from a lower limit of about 1%, 2%, 5%, 10%, or 15% to an upper limit of about 30%, 25%, 20%, or 10%, and wherein the amount of coalescing agent may range from any lower limit to any upper limit and encompass any subset between the upper and lower limits. In some embodiments, the coalescing agent may be a mixture of one or more Formula I coalescing agent derivatives and/or one or more additional coalescing agents.

In some embodiments, a coating formulation may comprise at least one additional coalescing agent. Suitable additional coalescing agents may be any known coalescing agent including, but not limited to, benzoic acid alkyl esters, ester-alcohols, glycol-ether type solvents, long-chain aliphatic alcohols, aromatic alcohols, and the like, and any combination thereof. Examples of benzoic acid alkyl esters include, but are not limited to, benzoic acid alkyl esters where the alkyl group, which can be straight or branched, substituted or unsubstituted, has from about 2 to about 30 carbon atoms, such as decyl or isodecyl benzoate, nonyl or isononyl benzoate, octyl or isooctyl benzoate, 2-ethylhexyl benzoate, tridecyl or isotridecyl benzoate, 3,7-dimethyloctyl benzoate, 3,5,5-trimethylhexyl benzoate, and the like, and any combination thereof. Specific commercial examples of such benzoic acid alkyl esters include VELTA® 262 (isodecyl benzoate, available from Velsicol Chemical Corporation) and VELTA® 368 (2-ethylhexyl benzoate, available from Velsicol Chemical Corporation). Examples of ester-alcohols include, but are not limited to, hydroxyalkyl esters of alkanoic acids where the alkyls group, which can be straight or branched, substituted or unsubstituted, independently have from about 2 to about 30 carbon atoms, such as 2,2,4-trimethylpentane-1,3-diol monoisobutyrate. Specific commercial examples of such ester-alcohols include TEXANOL® (2,2,4-trimethyl-1,3-pentanediol monoisobutyrate, available from Eastman). Examples of glycol-ether type solvents include diethylene glycol monomethylether acetate, diethylene glycol monobutylether acetate, butyl carbitol acetate (BCA), and the like, and any combination thereof. Specific commercial examples of such glycol-ether include butyl CELLOSOLVE® (ethylene glycol monobutyl ether, available from Dow Chemical). Examples of long-chain aliphatic alcohols include those where the alkyl group is from about 5 to about 20 carbon atoms, such as ethylhexanol, octanol, dodecanol, and the like. Examples of aromatic alcohols include benzyl alcohol, phenol, and the like.

In some embodiments, a solvent may be any solvent suitable for applying a coating that is compatible with a chosen coalescing agent. Examples of suitable solvents include, but are not limited to, water, alcohols, petroleum distillate, esters, glycol ethers, and any combination thereof. Most preferably the solvent may be water.

In some embodiments, a binder may be any binder suitable for use in a coating that is compatible with a chosen coalescing agent. Examples of suitable binders include, but are not limited to, resins, emulsion polymers, and any combination thereof.

Suitable resins for use as a binder include, but are not limited to, a polyester resin, an alkyd, an acrylic, a vinyl-acrylic, vinyl acetate/ethylene (VAE), a polyurethane, a melamine resin, an epoxy, a styrenic, a styrene-acrylic copolymer, a styrene-alkene copolymer, any derivative thereof, and any combination thereof.

Examples of suitable polyester resins include polymers prepared by the esterification of phthalic anhydride, isophthalic, terephthalic, adipic, or any other aromatic or aliphatic di- or tri-carboxylic acid with linear or branched aliphatic or aromatic alcohols, such as ethylene glycol, diethylene glycol, triethylene glycol, bisphenol A, any derivative thereof, and any combination thereof.

Alkyd resins, as used herein, refer to fatty acid-modified and oil-modified polyesters. Suitable alkyd resins may include, but are not limited to, polyesters of those listed above modified with a fatty acid or oil. Further, suitable alkyd resins may include, but are not limited to, acrylic-modified alkyd resins, sulfonated alkyd resins, and any combination thereof.

Examples of suitable acrylic resins may include, but not be limited to, resins with monomeric units of alkyl(meth)acrylates having 1 to 20 carbon atoms, such as methyl(meth)acrylate, ethyl(meth)acrylate, n-butyl(meth)acrylate, isobutyl(meth)acrylate, t-butyl(meth)acrylate, 2-ethylhexyl(meth)acrylate, and tridecyl(meth)acrylate; cycloalkyl(meth)acrylates having 4 to 20 carbon atoms, such as cyclohexyl(meth)acrylate, methylcyclohexyl(meth)acrylate, cyclododecyl(meth)acrylate, and t-butylcyclohexyl(meth)acrylate; aralkyl(meth)acrylates having 3 to 20 carbon atoms, such as allyl(meth)acrylate and benzyl(meth)acrylate; alkylcyclohexylalkyl esters of (meth)acrylic acid, such as 4-methylcyclohexylmethyl(meth)acrylate, 4-ethylcyclohexylmethyl(meth)acrylate, 4-methoxycyclohexylmethyl(meth)acrylate, 4-acetoxymethylcyclohexylmethyl(meth)acrylate, 3-methylcyclohexylmethyl(meth)acrylate, 3-ethylcyclohexylmethyl(meth)acrylate, 3-acetoxymethylcyclohexylmethyl(meth)acrylate, 3-hydroxymethylcyclohexylmethyl(meth)acrylate, 4-methylcyclohexylethyl(meth)acrylate, 3-methylcyclohexylethyl(meth)acrylate, 4-methylcyclohexypropyl(meth)acrylate, 3-methylcyclohexypropyl(meth)acrylate, 4-methylcyclohexybutyl(meth)acrylate, and 3-methylcyclohexybutyl(meth)acrylate; epoxy-group-containing vinylic monomers, such as glycidyl(meth)acrylate; hydroxyl-group-containing acrylic monomers, such as 2-hydroxyethyl(meth)acrylate, 2-hydroxypropyl(meth)acrylate, 4-hydroxybutyl(meth)acrylate, and (meth)acryloxypolyoxyalkylenes; α,β-ethylenically unsaturated carboxylic acids or unsaturated carboxylic anhydrides, such as acrylic acid, methacrylic acid, maleic acid, maleic anhydride, itaconic acid, itaconic anhydride, crotonic acid, fumaric acid, and citraconic acid; acid-group-containing (meth)acrylates, such as (meth)acryloxyethyl phosphate and (meth)acryloxyethylsulfonic acid; salts (e.g., alkaline metal salts, ammonium salts, amine salts) of the unsaturated carboxylic acids and the acid-group-containing (meth)acrylates; half esters between unsaturated carboxylic anhydrides (e.g., maleic anhydride) and linear or branched alcohols having 1 to carbon atoms; urethane-bond-containing urethane(meth)acrylate compounds such as reaction products between isocyanate-group-containing compounds and hydroxyalkyl(meth)acrylates; (meth)acryl-group-containing silicone macromers such as (meth)acryl-group-containing organopolysiloxanes such as γ-(meth)acryloyloxypropyltrimethoxysilane, γ-(meth)acryloyloxypropyltriethoxysilane, and γ-(meth)acryloyloxypropylmethyldimethoxysilane; basic unsaturated monomers, such as dimethylaminoethyl(meth)acrylate, diethylaminoethyl(meth)acrylate, dimethylaminoethyl(meth)acrylamide, and dimethylaminopropyl(meth)acrylamide; unsaturated sulfonic acids, such as 2-sulfoethyl(meth)acrylate and its salts; caprolactone-modified (meth)acrylic acids; amino-group-containing (meth)acrylates, such as t-butylaminoethyl(meth)acrylate, t-butylaminopropyl(meth)acrylate, aziridinylethyl(meth)acrylate, pyrrolidinylethyl(meth)acrylate, and piperidinylethyl(meth)acrylate; (meth)acrylamides, such as (meth)acrylamide, N-monomethyl(meth)acrylamide, N-monoethyl(meth)acrylamide, N,N-dimethyl(meth)acrylamide, N-methylol(meth)acrylamide, N-butoxy(meth)acrylamide, N-dimethylaminoethyl(meth)acrylamide, N-diethylaminoethyl(meth)acrylamide, N-dimethylaminopropyl(meth)acrylamide, and N-diethylaminopropyl(meth)acrylamide; monomers having more than one polymerizable unsaturated bonds, such as polyethylene glycol di(meth)acrylate, ethylene glycol di(meth)acrylate, propylene glycol di(meth)acrylate, neopentyl glycol di(meth)acrylate, 1,6-hexanediol di(meth)acrylate, and triallyl cyanurate; and polymerizable monomers containing a piperidinic group, such as 4-(meth)acryloyloxy-2,2,6,6-tetramethylpiperidine, 4-(meth)acryloylamino-2,2,6,6-tetramethylpiperidine, 4-(meth)acryloyloxy-1,2,2,6,6-pentamethylpiperidine, 4-(meth)acryloyloxy-1-methoxy-2,2,6,6-tetramethylpiperidine, 4-cyano-4-(meth)acryloyloxy-2,2,6,6-tetramethylpiperidine, 1-(meth)acryloyl-4-(meth)acryloylamino-2,2,6,6-tetramethylpiperidine, and 4-crotoylamino-2,2,6,6-tetramethylpiperidine.

Suitable polyurethane resins include thermoplastic polyurethane resins and thermosetting polyurethane resins. Further, suitable polyurethane resins may have a polyester, polycarbonate, or polyether backbone with an aliphatic isocyanate or aromatic isocyanate, and the like, and any combination thereof.

Examples of suitable epoxy resins include, but are not limited to, a Bisphenol A type epoxy such as EPON® Resin 828 (Bisphenol A/epichlorohydrin derived resin, available from Shell Chemical).

Suitable emulsion polymers for use as a binder in the present invention include, but are not limited to, cationic, anionic, amphoteric, and nonionic emulsion polymers. Examples of anionic emulsion polymers include polymers from one or more nonionic ethylenically unsaturated monomers, such as, for example, (meth)acrylic ester monomers including C1 to C18 alkyl(meth)acrylates, such as methyl(meth)acrylate, ethyl(meth)acrylate, butyl(meth)acrylate, 2-ethylhexyl(meth)acrylate; hydroxyethyl(meth)acrylate; acid functional monomers, such as (meth)acrylic acid, crotonic acid, itaconic acid, fumaric acid and maleic acid; monomethyl itaconate; monomethyl fumarate; monobutyl fumarate; maleic anhydride; acrylamide or substituted acrylamides; diacetone acrylamide; glycidyl methacrylate; acetoacetoxy ethyl methacrylate (AAEM); (meth)acrolein; isocyanatoalkyl(meth)acrylates; styrene or substituted styrenes; butadiene; ethylene; vinyl acetate or other vinyl esters; vinyl monomers, such as, vinyl halide; amine functional monomers, such as, for example, N,N'-dimethylamino(meth)acrylate; and (meth)acrylonitrile. Additional examples may include, but are not limited to, polymers formed from monomers of butyl acrylate, ethyl acrylate, ethyl hexyl(meth)acrylate, methyl methacrylate, styrene, styrene-butadiene, (di)acid monomer, amine-group containing monomer, any derivative thereof, and any combination thereof. A commercial example of an emulsion polymer may include ORGAL® (acrylic polymer emulsions, available from Organik Kimya).

In some embodiments, the binder may be present in the coating formulation in an amount that may range from a lower limit of about 15%, 20%, 25%, or 30% to an upper limit of about 60%, 55%, 50%, or 40%, and wherein the amount of binder may range from any lower limit to any upper limit and encompass any subset between the upper and lower limits. In some embodiments, the binder may be a mixture of one or more resins and/or one or more emulsion polymers.

In some embodiments, the coating formulation may include additional additives. Examples of suitable additives for the coating formulation include, but are not limited to, pigments, colorants and tints, surfactants, suspension additives, antifoaming agents, biocides, fungicides, particulates, cementitious compositions, texturizing compositions, aqueous-miscible solvents, pH adjusters, crosslinking agents, thickening agents, viscosifiers, fillers, freeze-thaw additives, flattening additives, pigment grind additives, opacifiers, stabilizers, film preservatives, and any combination thereof. It should be understood that the term "particulate" or "particle," as used in this disclosure, includes all known shapes of materials, including substantially spherical materials, fibrous materials, high-to-low aspect ratio materials, polygonal materials (such as cubic materials), and mixtures thereof.

Examples of suitable pigments may include any known pigment that would be compatible with the coalescing agent. Suitable pigments may be those known for use in paints, coatings, adhesives, inks, toners, sealants, stains, glazes, carpet backings, and primers. Suitable pigments may be organic or inorganic-based pigments or a combination thereof. Pigments may additionally provide a reflective surface. Examples of suitable inorganic pigments include, but are not limited to, titanium oxide in both the anastase and rutile forms; clay (aluminum silicate); calcium carbonate in both the ground and precipitated forms; aluminum oxide; silica (silicon dioxide); magnesium oxide; talc (magnesium silicate); barytes (barium sulfate); zinc oxide; zinc sulfite; sodium oxide; potassium oxide; and the like; and any combination thereof. Titanium dioxide is commonly used to provide paints with hiding power.

In some embodiments, it may be desirable to form a coating on a surface using an embodiment of the coating formulation as described. One skilled in the art, with the benefit of this disclosure, should understand the plurality of methods by which a coating may be applied including, but not limited to, spraying, painting, rolling, brushing, dip coating, layering, transferring, printing, and the like, and any combination thereof. Additionally, one skilled in the art, with the benefit of this disclosure, should recognize the plurality of materials and surfaces that may be coated including, but not limited to, plastics, polymers, composite materials, metals, metal-alloys, ceramics, glass, a natural material, wood, stucco, concrete, brick, stone, and the like, and any combination thereof. Further, one skilled in the art, with the benefit of this disclosure, would understand that R1 and R2 can be independently tailored, as well as the overall coating formulation, for a desired coating application method and surface to be coated.

In some embodiments, a final coating may be formed when an applied coating formulation has coalesced, dried, cured, crosslinked, polymerized, or any combination thereof. For simplicity, the term "coalescing," and derivatives thereof, is used to generally denote the process of drying, curing, crosslinking, polymerizing, or any combination thereof. As used herein, "final" is used as a descriptive term to denote a time point after at least 95% of coalescing has taken place and the coating film has achieved a minimum level of physical properties suitable for the intended application, such as, but not limited to, hardness representing dry-to-the-touch, recognizing that the ultimate steady state physical properties of the coating may not be reached for an extended period of time.

In some embodiments, R1 and R2 may be independently tailored and/or chosen to achieve a desired rate of coalescing. By way of nonlimiting example, a coalescing agent according to Formula I with a molecular weight of less than about 300 amu may dry faster than with a molecular weight of greater than 500 amu. Another nonlimiting example may include, a coalescing agent according to Formula I with an R group designed with a low molecular weight and reactive group, like $-(CH_2)_2CH=CH_2$, to allow for coalescence and polymerization coalescing mechanisms.

In some embodiments, R1 and R2 may be independently tailored to achieve a particular set of final coating properties. Nonlimiting examples of final coating properties that can be tailored include, but are not limited to, thickness; durability; flexibility; toughness; opaqueness or hiding effectiveness; gloss level, e.g., matte, eggshell, semi-gloss, or gloss; tackiness; block resistance; pigment brilliance; odor; thermal insulation; sound insulation; and hydrophobicity.

In some embodiments, a coalescing agent, according to an embodiment of Formula I, may provide for a coating with greater hiding power, higher hardness, increased block resistance, low odor, decreased dirt pickup, or any combination thereof.

While the embodiments have primarily referred to coating formulations, the embodiments may extend to other applications including, but not limited to, paints like craft paints, traffic paints, interior paints, roof paints, exterior paints, and the like; adhesives; inks; toners; caulks; sealants; stains; glazes; carpet backings; and primers. In some embodiments, a coating formulation may be included as part of a paint, a coating, an adhesive, an ink, a toner, a sealant, a stain, a glaze, a carpet backing, and a primer.

In some embodiments, a coalescing agent, according to an embodiment of Formula I, may be a component of a paint that is applied to an exterior structure via a spraying method.

In some embodiments, a coalescing agent, according to an embodiment of Formula I, may be a component of a sealant that is applied to a cementitious surface to provide a water-resistant coating.

In some embodiments, a coalescing agent according to an embodiment of Formula I may be a component of a pressure-sensitive adhesive formulation applied to a substrate to produce a tape or a label.

In some embodiments, a composition may generally include a binder; a solvent; and a coalescing agent according to Formula I, where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof.

In one embodiment, a composition may further comprise an additive selected from the group consisting of a pigment, a pigment extender, a colorant, a tint, a dye, a surfactant, a suspension additive, an antifoaming agent, a biocide, a fungicide, a particulate, a cementitious composition, a texturizing composition, a water-miscible solvent, a pH adjuster, a crosslinking agent, a thickening agent, a viscosifier, a filler, a freeze-thaw additive, a flattening additive, a pigment grind additive, an opacifier, a stabilizer, a film preservative, and any combination thereof.

In one embodiment, a composition may further comprise at least one additional coalescing agent.

In one embodiment, a composition may have a coalescing agent of Formula I where R1 and R2 are different.

In one embodiment, a composition may have a coalescing agent of Formula I where R1 and R2 are the same.

In one embodiment, a composition may have a coalescing agent with at least one of R1 and R2 comprise a heteroatom.

In one embodiment, a composition may have a coalescing agent with at least one of R1 and R2 comprise a cyclic structure. Further, the cyclic structure may be aromatic.

In one embodiment, a composition may have a coalescing agent with at least one of R1 and R2 comprise a reactive group. Further, the reactive group may be an olefin, a carboxylic acid, an alcohol, an epoxide, a cyanate, an amine, a silane, an epoxy-silane, a heteroatom, and any combination thereof. Further, the reactive group may be a reactive group capable of undergoing a reaction selected from the group consisting of an addition reaction, a condensation reaction, a ring-opening reaction, a free-radical reaction, and any combination thereof.

In one embodiment, a composition may have a coalescing agent with a molecular weight between about 300 amu and about 750 amu.

In one embodiment, a composition may have a binder being a resin of an alkyd, an acrylic, a vinyl-acrylic, vinyl acetate/ethylene (VAE), a polyurethane, a polyester, a melamine resin, an epoxy, a styrene, a styrene-acrylic copolymer, a styrene-alkene copolymer, any derivative thereof, and any combination thereof.

In one embodiment, a composition may have a binder as an emulsion polymer. In one embodiment, a composition may have a coalescing agent present at about 2% to about 30% by weight of the composition. In one embodiment, a composition may have a coalescing agent with the binder present at about 15% to about 60% by weight of the composition.

In one embodiment, a composition may have a solvent of water, petroleum distillate, an ester, a glycol ether, and any combination thereof.

In one embodiment, a composition may have a volatile organic content less than about 500 g/L.

In some embodiments, a product may be a paint, a coating, an adhesive, an ink, a toner, a sealant, a stain, a glaze, a carpet backing, or a primer that includes a composition according to Formula I where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof.

In one embodiment, a coating may be formed by a process selected from the group consisting of coalescing, drying, curing, crosslinking, polymerizing, and any combination thereof.

In one embodiment, a coating may further include an additive selected from the group consisting of a pigment, a pigment extender, a colorant, a tint, a dye, a surfactant, a suspension additive, an antifoaming agent, a biocide, a fungicide, a particulate, a cementitious composition, a texturizing composition, a water-miscible solvent, a pH adjuster, a crosslinking agent, a thickening agent, a viscosifier, a filler, a freeze-thaw additive, a flattening additive, a pigment grind additive, an opacifier, a stabilizer, a film preservative, and any combination thereof.

In one embodiment, a coating may have a coalescing agent with at least one of R1 and R2 comprise a reactive group. In one embodiment, a composition may have a binder being an emulsion polymer.

In some embodiments, a composition may generally include a binder; a solvent; a coalescing agent according to Formula I where Z can be $C_1$-$C_{10}$, (i) X is —H and Y is =O or (ii) X is =O and Y is —H or —$CH_3$, and R1 and R2 are independently selectable and comprise a $C_1$-$C_{12}$ or derivative thereof. In some embodiments, a composition may be applied to a surface so as to form a coating.

Embodiments of coalescing agents of the present invention disclosed herein include those according to Formula I with where Z can be $C_1$-$C_{10}$ (e.g., linear, branched, comprise at least one unsaturated C—C bond, comprise at least one cyclic group, comprise at least one aromatic group, and any combination thereof), where (i) X is —H and Y is =O or (ii) X is =O and Y is —H or —$CH_3$, and where R1 and R2 are independently selectable and comprise a $C_1$-$C_{12}$ or derivative thereof (e.g., linear with a terminal or internal bond to Formula I, branched, cyclic, aromatic, include an unsaturated bond, include heteroatoms, include a reactive group, or a combination thereof). Further, as discussed further herein, the coalescing agents (or combinations of coalescing agents) may be used in compositions of the present invention that comprise binders, solvents, optionally additional coalescing agents, optionally pigments, optionally colorants, optionally tints, optionally surfactants, optionally suspension additives, optionally antifoaming agents, optionally biocides, optionally fungicides, optionally particulates, optionally cementitious compositions, optionally texturizing compositions, optionally aqueous-miscible solvents, optionally pH adjusters, optionally crosslinking agents, optionally thickening agents, optionally viscosifiers, optionally fillers, optionally freeze-thaw additives, optionally flattening additives, optionally pigment grind additives, optionally opacifiers, optionally stabilizers, optionally film preservatives, and any combination thereof, including any examples disclosed herein of each of the foregoing components of the compositions.

In some embodiments, a composition may include a binder (e.g., acrylic, vinyl acrylic, styrene acrylic, ethylene vinyl acrylic, styrene/butadiene, and styrenics), a coalescing agent of the present invention (e.g., according to any of the embodiments of Formula I as disclosed herein), a solvent (e.g., water), optionally additional coalescing agents (e.g., according to any embodiments of Formula I as disclosed herein and additional coalescing agents as disclosed herein), optionally pigments (e.g., titanium dioxide), optionally pigment extenders (e.g., calcium carbonate and other mineral fillers), optionally tints, optionally colorants, optionally dyes, optionally surfactants, optionally rheology modifiers, optionally thickeners, optionally biocides, and optionally freeze thaw additives.

To facilitate a better understanding of the present invention, the following examples of preferred embodiments are given. In no way should the following examples be read to limit, or to define, the scope of the invention.

EXAMPLES

Coalescing Agent:

A coalescing agent, di-octylsuccinate of Formula I in which X is =O and Y is H, and R1 and R2 are 1-ethylpentyl was produced by the esterification of succinic acid with 2-ethylhexanol in the presence of an acidic catalyst.

Measurement Procedures:

The viscosity behavior of each formulation was tested using a BYK-Gardner KU+1 viscometer with a paddle type spindle. All viscosity measurements were made at a constant temperature of 25° C. Viscosity measurements are present in Krebs units (KU).

The solids content (% wt) was determined according to ASTM D2369.

Dry film gloss and contrast ratios were measured in triplicate on drawdown films applied over BYK opacity charts in a wet film thickness of 3 mils. Gloss measurements were taken using a BYK-Gardner micro-TRI-gloss meter at 25°, 60°, and 85°. The contrast ratio was determined using a handheld Mercury Datacolor colorimeter.

Sag and leveling draw-downs were made on BYK opacity charts and visually analyzed after 24 hours of drying.

Block testing was performed according to ASTM D4946 and rated on a scale of 0-10, where 0 is a complete fail and 10 is a perfect pass.

The volatile organic content (VOC) and GC retention times for coalescing agents were determined using ASTM D6886, unless specified as calculated where the following formula was used.

$$VOC = (f_V - f_W) D_P$$

where:
$f_V$ is the weight fraction of total volatile content (1−weight fraction of solids content)
$f_W$ is the weight fraction of water content
$D_P$ is the density of the paint in g/L The scrub resistance was tested according to ASTM D2486.

The low temperate coalescent (LTC) procedure followed ASTM D7306. The rankings of the draw-downs followed the rating system of ASTM D7306 with 5 indicating no cracking and 0 indicating the film chipped off completely.

Example 1

A clear concrete sealer formulation (Sealer 1) was prepared using coalescing agent di-octyl succinate described above. The clear concrete sealer formulation was prepared to a final composition as outlined in Table 1. Further, the properties of a coating formed from the sealer are provided in Table 1.

TABLE 1

|  | Sealer 1 |
| --- | --- |
| Raw Materials (lbs) | |
| water | 131.50 |
| ethylene glycol | 7.87 |
| ORGAL ® P086V (styrene-acrylic copolymer) | 344.30 |
| AGITAN ® 731 (siloxane defoamer) | 3.94 |
| DEIONIC ® LF 80 MOD (wetting agent) | 2.96 |
| di-octyl succinate | 17.71 |
| ammonia | 2.96 |
| boar-defense (anti-fouling agent) | 3.50 |
| Properties | |
| VOC (g/L) | 95.74 |
| Gloss at 60 | 80-90 |
| Viscosity | 34 sec |
| lb/gal | 8.59 |

Example 2

Two paint formulations were prepared using coalescing agent di-octyl succinate described above. The paint formulations were prepared to the final compositions outlined in Table 2. The preparation included combining the water (first listing), ethylene glycol, TAMOL® 731A, DEIONIC® LF 80MOD, AMP® 75, and DEE FO® 3010A in a stainless steel beaker with an Eiger Mixer (Model 1110SC). Then TAFIGEL PUR® 80 was added under agitation at 1000 rpm. After about a minute of agitation, the MINEX® 10, MINEX® 4, and ATTAGEL® 50 were mixed in at 1400 rpm for about 15 minutes to achieve a Hegman Fineness of Grind rating between about 6 and about 7. The rpm of the agitator was then adjusted as needed to maintain a vortex and the rinse water was added. Then the agitator speed was reduced to about 1000 rpm and the remaining ingredients (the letdown materials) were added over a period of about 10 minutes in the order listed below.

The properties of coatings formed from the paints are provided in Table 2.

TABLE 2

|  | Paint 1 | Paint 2 |
| --- | --- | --- |
| Mill Grind Materials (lbs) | | |
| water | 29 | 55 |
| ethylene glycol | — | 12 |
| TAMOL ® 731A (a scale inhibitor, available from Rohm and Haas) | 8 | 9 |
| DEIONIC ® LF 80 MOD (a wetting agent, available from DeForest Enterprises) | 2 | 3.5 |
| AMP ® 75 (a multifunctional amine, available from Dow) | — | 1.5 |
| DEE FO ® 3010 A (an oil-based defoamer, available from Munzing) | 0.5 | 1 |
| TAFIGEL PUR ® 80 (a thickener, available from Munzing) | 17 | — |
| MINEX ® 10 (sodium-potassium alumina silicate, available from Unimin Corporation) | 50 | 70 |
| MINEX ® 4 (sodium-potassium alumina silicate, available from Unimin Corporation) | — | 115 |
| ATTAGEL ® 50 (a thickener, available from BASF) | 3 | — |
| Rinse Material (lbs) | | |
| water | 81 | 25.37 |
| Letdown Materials (lbs) | | |
| TiO₂ slurry | 280 | 250 |
| water | 80 | 75 |
| TAFIGEL ® PUR 80 | 12 | 20 |
| ROPAQUE ™ ULTRA (an opaque polymer, available from Dow) | 60 | 40 |
| ORGAL ™ P850 RR (an acrylic, available from SteraChemicals) | 410 | 415 |
| di-octyl succinate | 10 | 10 |
| DEE FO ® 3010 A | 1.5 | 3 |
| TAFIGEL PUR ® 61 (a thickener, available from Munzing) | 10 | — |
| TAFIGEL PUR ® 41 (a thickener, available from Munzing) | — | 7 |
| Properties | | |
| VOC (g/L) | 4 | 40 |
| Viscosity | 107 | 100 |
| ICI | 1.21 | 1.175 |
| pH | 8.7 | 9.2 |
| Gloss at 60 | 42.7 | n.m. |
| Sheen at 85 | n.m. | 9.4 |
| Contrast Ratio/Y Reflectance | 97.98 | 97.24 |
| Green Alkyd Adhesion (3 day dry) | 5B/5B | 5B/5B |
| Block (RT/120° F.) (O.N.) | 6/3 | 7/4 |
| Block (RT/120° F.) (7 days) | 6/3 | 10/8 |
| Scrub Resistance (cycles) | 503 | 649 |
| Freeze/Thaw | failed | +10 ku/+20 ku |
| Oven Stability (10 days at 120° F.) | +4 ku | +7 ku |

Example 3

A master semi-gloss paint formulation was prepared with the composition of SG1 and SG2 in Table 3 below without the "Coalescing Agent."

TABLE 3

| SG1 | |
|---|---|
| water | 188 |
| TAMOL ® 731 A | 8 |
| DEIONIC ® LF 80 MOD | 2 |
| DEE FO ® 3010 A | 0.5 |
| TAFIGEL PUR ® 80 | 19.7 |
| MINEX ® 10 | 50 |
| ATTAGEL ® 50 | 3 |
| TiO$_2$ slurry | 280 |
| ROPAQUE ™ ULTRA | 60 |
| ORGAL ™ P850 RR | 410 |
| DEE FO ® 3010 A | 1.5 |
| TAFIGEL PUR ® 61 | 1.3 |
| "Coalescing Agent" | 10 |
| SG2 | |
| water | 135.6 |
| propylene glycol | 34.6 |
| TiO$_2$ slurry | 325.5 |
| KATHON ™ LX 1.5% (a microbicide, available from Dow) | 1.8 |
| RHOPLEX ™ SG-30 (an acrylic emulsion, available from Dow) | 501.4 |
| AEROSOL ® OT-25 (a surfactant, available from Cytec Industries Inc.) | 1.5 |
| BYK-002 (a defoamer available from BYK Chemie) | 2.1 |
| ammonia (28%) | 1.0 |
| ACRYSOL ™ RM-2020 NPR (a thickener, available from Dow) | 12.2 |
| ACRYSOL ™ SCT-275 (a thickener, available from Dow) | 10.2 |
| "Coalescing Agent" | 12.5 |

* All measurements in parts by weight.

Then the master semi-gloss paint formulation was measured into pint-sized cans where the five coalescing agents below were added separately in amounts to achieve the concentration in Table 3.

(CA1) di-octyl succinate
(CA2) trimethylpentanediol monoisobutyrate (TEXANOL®)
(CA3) 2,2,4-trimethyl-1,3-pentanediol diisobutyrate
(CA4) OPTIFILM® 400 (a very low VOC coalescent, available from Eastman)
(CA5) dipropylene glycol-n-butyl ether Several physical and performance characteristics of the samples were measured (measurement methods described above) and are provided in Table 4 below.

TABLE 4

| Property | SG1-CA1 | SG1-CA2 | SG1-CA3 | SG1-CA4 | SG1-CA5 |
|---|---|---|---|---|---|
| Initial Viscosity (KU) | 94.5 | 92.6 | 97.1 | 94.7 | 108.3 |
| 24-hour Viscosity (KU) | 103.6 | 99.4 | 103.8 | 102.6 | 114.6 |
| Solids (wt %) | 48.14 ± 0.03 | 48.03 ± 0.08 | 48.43 ± 0.93 | 49.08 ± 0.06 | 48.11 ± 0.09 |
| Density (g/L) | 1252.99 | 1260.42 | 250.11 | 1250.59 | 1244.36 |
| VOC* (g/L) | <4 | <50 | <50 | <50 | <50 |
| Sag | 5.0 ± 0.0 | 4.7 ± 0.6 | 2.0 ± 0.0 | 2.7 ± 0.6 | 7.7 ± 0.6 |
| Leveling | 4.0 ± 0.0 | 3.3 ± 0.6 | 3.7 ± 0.6 | 3.0 ± 0.0 | 4.0 ± 0.0 |
| Contrast Ratio | 94.35 ± 1.50 | 93.97 ± 0.57 | 94.52 ± 0.42 | 93.86 ± 1.17 | 95.23 ± 0.19 |
| G20° | 2.27 ± 0.06 | 2.13 ± 0.06 | 2.17 ± 0.06 | 2.40 ± 0.00 | 3.33 ± 0.06 |
| G60° | 16.60 ± 0.17 | 15.67 ± 0.21 | 15.77 ± 0.25 | 17.47 ± 0.21 | 23.53 ± 0.49 |
| G85° | 61.87 ± 0.74 | 65.07 ± 3.91 | 62.73 ± 1.57 | 63.90 ± 0.70 | 67.83 ± 1.81 |
| Block Resistance | 2.33 ± 1.15 | 2.33 ± 0.58 | 2.67 ± 0.58 | 2.67 ± 0.58 | 1.00 ± 0.00 |
| Scrub Resistance Rankings | 8 | 8 | 9 | 9 | 7.5 |
| LTC Rankings (10 mil film) | 0 | 0 | 0 | 0 | 2 |
| LTC Rankings (5 mil film) | 0 | 1 | 1 | 1 | 2 |

| Property | SG2-CA1 | SG2-CA2 | SG2-CA3 | SG2-CA4 | SG2-CA5 |
|---|---|---|---|---|---|
| Initial Viscosity (KU) | 97.8 | 96.4 | 100.3 | 98.3 | 86.6 |
| 24-hour Viscosity (KU) | 106.6 | 103.2 | 106.8 | 104.7 | 100.9 |
| Solids (wt %) | 48.44 ± 0.08 | 47.63 ± 0.07 | 48.01 ± 0.10 | 48.71 ± 0.02 | 47.79 ± 0.08 |
| Density (g/L) | 1245.32 | 1244.96 | 1243.64 | 1242.69 | 1241.49 |
| VOC* (g/L) | <104 | <150 | <150 | <150 | <150 |
| Sag | 10.7 ± 1.2 | 10.0 ± 0.0 | 11.3 ± 0.6 | 10.7 ± 0.6 | 7.3 ± 0.6 |
| Leveling | 4.0 ± 0.0 | 4.0 ± 0.0 | 4.0 ± 0.0 | 4.0 ± 0.0 | 3.8 ± 0.3 |
| Contrast Ratio | 96.24 ± 0.41 | 96.25 ± 0.37 | 96.43 ± 0.21 | 96.98 ± 0.20 | 96.40 ± 0.68 |
| G20° | 44.43 ± 1.05 | 39.83 ± 0.40 | 39.80 ± 0.44 | 45.53 ± 0.40 | 37.43 ± 1.24 |
| G60° | 74.43 ± 5.79 | 75.33 ± 0.25 | 75.07 ± 0.21 | 78.03 ± 0.32 | 73.27 ± 1.19 |
| G85° | 97.93 ± 0.32 | 97.83 ± 0.21 | 97.57 ± 0.51 | 98.23 ± 0.12 | 96.23 ± 0.40 |
| Block Resistance | 5.00 ± 0.00 | 6.00 ± 0.00 | 5.33 ± 0.58 | 5.67 ± 0.58 | 6.00 ± 0.00 |
| Scrub Resistance Rankings | 8 | 8 | 9 | 9 | 8 |

TABLE 4-continued

| | | | | | |
|---|---|---|---|---|---|
| LTC Rankings (10 mil film) | 5 | 5 | 5 | 5 | 5 |
| LTC Rankings (5 mil film) | 5 | 5 | 5 | 5 | 5 |

*calculated VOC

A fresh set of five samples were prepared to test the tinting viscosity with different tinting formulations. The Tinting Strength (uncorrected) was calculated according to the ASTM method D4286. The red, blue, and yellow color concentrates were obtained from the Universal Color Corporation. The tint strength tests samples were prepared with 20 g of white paint and 2.5 g of colorant. The colorant in the paint was mixed with a Thinky-ARE-100 Mixer for 2 minutes. Two draw-downs were made of each sample where each drawdown contained a sample paint film on the left side and a standard paint film on the right side. Calculations of the tint strength (expressed in terms of % $TS_{UC}$) was performed following the procedure in ASTM D4286.

TABLE 5

| | No Coalescent | SG1-CA1 | SG1-CA2 | SG1-CA3 | SG1-CA4 | SG1-CA5 |
|---|---|---|---|---|---|---|
| Initial Viscosity (KU) | 100.0 | 102.6 | 103.5 | 106.0 | 105.7 | 87.5 |
| 24-Hour Viscosity (KU) | 115.5 | 104.3 | 108.4 | 108.6 | 107.8 | 95.2 |
| % $TS_{UC}$ RED | 99.4 | 80.2 | 99.8 | 87.9 | 85.5 | 101.1 |
| % $TS_{UC}$ YELLOW | 101.3 | 115.2 | 99.9 | 88.9 | 96.9 | 97.7 |
| % $TS_{UC}$ BLUE | 100 | 114.8 | 100.4 | 119.7 | 79.4 | 108.2 |
| | No Coalescent | SG2-CA1 | SG2-CA2 | SG2-CA3 | SG2-CA4 | SG2-CA5 |
| Initial Viscosity (KU) | 80.4 | 87.9 | 90.7 | 99.3 | 94.7 | 83.8 |
| 24-Hour Viscosity (KU) | 103.6 | 104.2 | 107.8 | 115.7 | 112.3 | 95.4 |
| % $TS_{UC}$ RED | 103.5 | 103.3 | 99.8 | 104.3 | 100.8 | 97.1 |
| % $TS_{UC}$ YELLOW | 100.2 | 83.5 | 99.4 | 80.1 | 74.3 | 90.1 |
| % $TS_{UC}$ BLUE | 97.7 | 101.4 | 100 | 105.8 | 99.7 | 80.5 |

These examples demonstrate that the succinate ester coalescing agent solvent performs as well as coatings prepared using conventional coalescing solvents, yet contribute no VOCs to the total VOC of the formulation.

Example 4

A master mill grind was prepared according to the formulation in Table 6 below. Then the required amount of master mill grind was added to ten pint-sized cans. To the cans, the rest of the formulation was added according to the formulation in Table 6, where the "Latex Composition" is one of the following four.

(L1) RHOPLEX™ SG-30 (all-acrylic latex, available from DOW Coating Materials)
(L2) STYROPHAN® ND 593 (styrene-butadiene latex, available from BASF)
(L3) ACRONAL® S504 (styrene-acrylic latex, available from BASF)
(L4) ACRONAL® 296D (styrene-acrylic latex, available from BASF)

TABLE 6

| | L1-D | L2-D | L3-D | L4-D |
|---|---|---|---|---|
| Mill Grind Materials (lbs) | | | | |
| water | 29 | 29 | 29 | 29 |
| TAMOL ® 731 A | 8 | 8 | 8 | 8 |
| DEIONIC ® LF 80 MOD | 2 | 2 | 2 | 2 |
| DEE FO ® 3010 A | 0.5 | 0.5 | 0.5 | 0.5 |
| TAFIGEL PUR ® 80 | 3.7 | 3.7 | 3.7 | 3.7 |
| MINEX ® 10 | 50 | 50 | 50 | 50 |
| ATTAGEL ® 50 | 3 | 3 | 3 | 3 |
| Rinse Material (lbs) | | | | |
| water | 81 | 81 | 81 | 81 |
| Letdown Materials (lbs) | | | | |
| TiO₂ slurry | 280 | 280 | 280 | 280 |
| water | 80 | 80 | 80 | 80 |
| TAFIGEL ® PUR 80 | 2.6 | 2.6 | 2.6 | 2.6 |
| ROPAQUE ™ ULTRA | 60 | 60 | 60 | 60 |
| "Latex Composition" | 410 | 410 | 410 | 410 |
| di-octyl succinate | 10 | 10 | 10 | 10 |
| DEE FO ® 3010A | 1.5 | 1.5 | 1.5 | 1.5 |
| TAFIGEL PUR ® 61 | 1.9 | 2.1 | 2.1 | 0.8 |
| | L1-T | L2-T | L3-T | L4-T |
| Mill Grind Materials (lbs) | | | | |
| water | 29 | 29 | 29 | 29 |
| TAMOL ® 731 A | 8 | 8 | 8 | 8 |
| DEIONIC ® LF 80 MOD | 2 | 2 | 2 | 2 |
| DEE FO ® 3010 A | 0.5 | 0.5 | 0.5 | 0.5 |
| TAFIGEL PUR ® 80 | 3.7 | 3.7 | 3.7 | 3.7 |
| MINEX ® 10 | 50 | 50 | 50 | 50 |
| ATTAGEL ® 50 | 3 | 3 | 3 | 3 |
| Rinse Material (lbs) | | | | |
| water | 81 | 81 | 81 | 81 |
| Letdown Materials (lbs) | | | | |
| TiO₂ slurry | 280 | 280 | 280 | 280 |
| water | 80 | 80 | 80 | 80 |
| TAFIGEL ® PUR 80 | 2.6 | 2.6 | 2.6 | 2.6 |
| ROPAQUE ™ ULTRA | 60 | 60 | 60 | 60 |
| "Latex Composition" | 410 | 410 | 410 | 410 |
| TEXANOL ® | 10 | 10 | 10 | 10 |
| DEE FO ® 3010 A | 1.5 | 1.5 | 1.5 | 1.5 |
| TAFIGEL PUR ® 61 | 1.9 | 2.1 | 2.9 | 0.7 |

TABLE 7

| Property | L1-D | L2-D | L3-D | L4-D |
|---|---|---|---|---|
| Initial Viscosity (KU) | 102.3 | 91.3 | 92.3 | 80.1 |
| 24-hour Viscosity (KU) | 103.8 | 95.3 | 94.3 | 108.8 |
| Solids (wt %) | 50.213 ± 0.001 | 50.109 ± 0.02 | 50.208 ± 0.004 | 50.745 ± 0.001 |
| Density (g/L) | 1260.42 | 250.11 | 1250.59 | 1244.36 |
| VOC* (g/L) | <4 | <4 | <4 | <4 |
| LTC Rankings (10 mil film) | 4 | 5 | 5 | 5 |
| LTC Rankings (5 mil film) | 5 | 5 | 5 | 5 |

| Property | L1-T | L2-T | L3-T | L4-T |
|---|---|---|---|---|
| Initial Viscosity (KU) | 96.1 | 90.3 | 93.1 | 84.3 |
| 24-hour Viscosity (KU) | 98.2 | 92.8 | 95.2 | 105.8 |
| Solids (wt %) | 50.172 ± 0.002 | 49.983 ± 0.000 | 50.446 ± 0.004 | 50.643 ± 0.003 |
| Density (g/L) | 1330.62 | 1302.59 | 1316.24 | 1303.30 |
| VOC* (g/L) | <50 | <50 | <50 | <50 |
| LTC Rankings (10 mil film) | 3 | 5 | 5 | 5 |
| LTC Rankings (5 mil film) | 4 | 5 | 5 | 5 |

*calculated VOC

The results show that the coalescing solvents of the present invention are suitable as coalescing solvents for a variety of emulsion polymer systems.

Example 5

The freezing point of di-octyl succinate is below about −18.5° C. The freezing point of the diester formed from a reaction between succinic acid and a 50/50 mixture of n-octanol and n-decanol has a measured melting point of about 6° C. Therefore, the branched material may have a broader freezing point range, which may advantageously allow for handling, storage, transportation, and application over a broader range of temperatures.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:
1. A composition comprising:
   a binder;
   bis(2-ethylhexyl)succinate as a biobased coalescing agent;

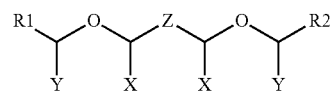

and
   a solvent wherein the composition has a volatile organic content less than about 500 g/L and the composition is used in a product selected from the group consisting of a paint, a coating, an adhesive, an ink, a toner, a sealant, a stain, a glaze, a carpet and a primer.
2. The composition of claim 1, wherein the coalescing agent is formed from a reaction between an alcohol and a biobased carboxylic acid.
3. A composition comprising:
   a binder;
   a biobased coalescing agent with the general formula of

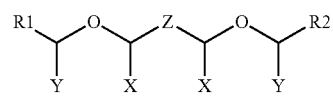

wherein Z is $C_2$, wherein X is =O and Y is —H or —$CH_3$ or —$CH_2CH_3$ or —$(CH_2)_2CH_3$ or derivative thereof, and wherein R1 and R2 are independently selectable and comprise a $C_5$-$C_{11}$ or derivative thereof and bonded on an interior carbon so as to form a branched structure and at least one of said R1 and R2 comprises a reactive group; and a solvent wherein the composition has a volatile organic content less than about 500 g/L and the composition is used in a product selected from the group consisting of a paint, a coating, an adhesive, an ink, a toner, a sealant, a stain, a glaze, a carpet and a primer.

4. The composition of claim 3, wherein the reactive group is selected from the group consisting of an olefin, a carboxylic acid, an alcohol, an epoxide, a cyanate, an amine, a silane, an epoxy-silane, a heteroatom, and any combination thereof.

5. The composition of claim 3, wherein the reactive group is capable of undergoing a reaction selected from the group consisting of an addition reaction, a condensation reaction, a ring-opening reaction, a free-radical reaction, and any combination thereof.

6. The composition of claim 1, further comprising at least one additional coalescing agent wherein the additional coalescing agent is a derivative of one selected from a group consisting of a succinic acid, adipic acid, sebacic acid, malonic acid, glutaric acid, pimelic acid, suberic acid, azelaic acid, ortho-phthalic acid, iso-phthalic acid, terephthalic acid, maleic acid, fumaric acid, glutaconic acid, traumatic acid, muconic acid, 1,4-butanediol, and resorcinol.

7. The composition of claim 1 further comprising:

an additive selected from the group consisting of a pigment, a pigment extender, a colorant, a tint, a dye, a surfactant, a suspension additive, an antifoaming agent, a biocide, a fungicide, a particulate, a cementitious composition, a texturizing composition, a water-miscible solvent, a pH adjuster, a crosslinking agent, a thickening agent, a viscosifier, a filler, a freeze-thaw additive, a flattening additive, a pigment grind additive, an opacifier, a stabilizer, a film preservative, and any combination thereof.

8. The composition of claim 1, wherein the binder is a resin selected from the group consisting of an alkyd, an acrylic, a vinyl-acrylic, vinyl acetate/ethylene (VAE), a polyurethane, a polyester, a melamine resin, an epoxy, a styrene, a styrene-acrylic copolymer, a styrene-alkene copolymer, any derivative thereof, and any combination thereof.

9. The composition of claim 1, wherein the solvent is selected from the group consisting of water, petroleum distillate, an ester, a glycol ether, and any combination thereof.

10. A method comprising:
providing a composition that comprises:
bis(2-ethylhexyl)succinate as a biobased coalescing agent;

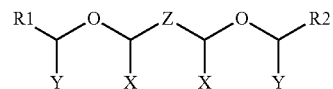

a binder; and a solvent wherein the composition has a volatile organic content less than about 500 g/L and the composition is used in a product selected from the group consisting of a paint, a coating, an adhesive, an ink, a toner, a sealant, a stain, a glaze, a carpet and a primer; and applying the composition to a surface so as to form a coating.

11. A composition comprising:
a binder selected from the group consisting of an acrylic, a vinyl acrylic, a styrene acrylic, an ethylene vinyl acrylic, a styrene/butadiene, and a styrenic;
bis(2-ethylhexyl)succinate as a coalescing agent

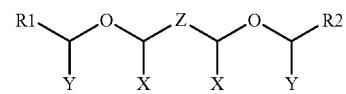

a solvent wherein the composition has a volatile organic content less than about 500 g/L; and at least one additive selected from the group consisting of a pigment, a pigment extender, a tint, a colorant, a surfactant, a rheology modifier, a thickener, a biocide, a freeze thaw additive, and any combination thereof.

12. The composition of claim 11, wherein the coalescing agent is biobased.

13. The composition of claim 11, wherein the coalescing agent is formed from a reaction between an alcohol and a biobased carboxylic acid.

14. The composition of claim 11, further comprising at least one additional coalescing agent.

15. The composition of claim 14, wherein at least one of the additional coalescing agents is a derivative of one selected from the group consisting of a succinic acid, adipic acid, sebacic acid, malonic acid, glutaric acid, pimelic acid, suberic acid, azelaic acid, ortho-phthalic acid, iso-phthalic acid, tere-phthalic acid, maleic acid, fumaric acid, glutaconic acid, traumatic acid, muconic acid, 1,4-butanediol, and resorcinol.

16. A product comprising the composition according to claim 11, wherein the product is selected from the group consisting of a paint, a coating, an adhesive, an ink, a toner, a sealant, a stain, a glaze, a carpet backing, and a primer.

* * * * *